(12) United States Patent
Kleiber et al.

(10) Patent No.: US 6,270,965 B1
(45) Date of Patent: *Aug. 7, 2001

(54) INTEGRATED METHOD AND SYSTEM FOR AMPLIFYING AND FOR DETECTING NUCLEIC ACIDS

(75) Inventors: Jörg Kleiber, Penzberg; Karim Tabiti, München; Gregor Sagner, Penzberg, all of (DE)

(73) Assignee: Roche Diagnostics, GmbH, Mannheim (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/115,906

(22) Filed: Jul. 15, 1998

(30) Foreign Application Priority Data

Jul. 15, 1997 (DE) .............................. 197 30 359

(51) Int. Cl.[7] .............................. C12Q 1/68; C12Q 1/70; C12P 19/34; G01N 33/53; C07H 21/04
(52) U.S. Cl. .................................. 435/6; 435/5; 435/7.1; 435/7.2; 435/91.2; 536/24.3; 935/77; 935/78
(58) Field of Search .................................. 435/6, 5, 91.2, 435/7.1, 7.2

(56) References Cited

U.S. PATENT DOCUMENTS

| | | | |
|---|---|---|---|
| 5,599,668 | * | 2/1997 | Stimpson et al. .......................... 435/6 |
| 5,750,337 | * | 5/1998 | Squirrell .................................. 435/6 |

FOREIGN PATENT DOCUMENTS

WO 94/02634 * 2/1994 (WO) ........................................ 435/6

OTHER PUBLICATIONS

Hlguchi et al., "Simultaneous Amplification and Detection of Specific DNA sequences ", Biotechnology, vol. 10, pp., 413–417, Apr. 1992.*

* cited by examiner

Primary Examiner—W. Gary Jones
Assistant Examiner—Arun K. Chakrabarti
(74) Attorney, Agent, or Firm—Arent Fox Plotkin Kintner Kahn PLLC.

(57) ABSTRACT

The present invention concerns a method and a device which enables an integrated amplification and detection of nucleic acids.

16 Claims, No Drawings

INTEGRATED METHOD AND SYSTEM FOR AMPLIFYING AND FOR DETECTING NUCLEIC ACIDS

The present invention concerns a method and a device which enables an integrated amplification and detection of nucleic acids.

Heterogeneous methods for the detection of nucleic acids include the step of immobilizing the nucleic acid to be detected. This can for example take place directly by covalent binding of the nucleic acid to a solid phase or by coupling the nucleic acid to a partner of an affinity pair and binding the other partner of the affinity pair to a solid phase. A further method of coupling is also to immobilize the nucleic acid to be detected by means of hybridization to a solid-phase-bound so-called capture probe which is at least partially complementary to the nucleic acid to be detected. This capture probe can be bound or become bound to a solid phase in any desired manner.

Examples of methods in which nucleic acids to be detected are immobilized by means of capture probes are described in EP-A-0 078 139 for direct binding and in EP-A-0 192 168 for binding via an affinity pair. In the procedures described in these references the nucleic acid to be detected is hybridized with a detection probe which can also hybridize with the nucleic acid to be detected and, after removing excess detection probe, the hybrid formed is detected on the solid phase by means of a marker group of the detection probe. In order to detect nucleic acids which occur rarely in a sample, a target-specific amplification is usually carried out. Such a method in which for example a digoxigenin marker group is incorporated into the amplified nucleic acid is described in WO92/06216.

In previous conventional methods in nucleic acid diagnostics the amplification and detection of nucleic acids was carried out in separate systems so that the products produced by amplification came into contact with the surroundings before the detection. This resulted in a high risk of cross-contaminations and false-positive results. In addition it was necessary to carry out several pipetting steps and at least one transfer step.

A combined amplification and detection method in a closed system is known from U.S. Pat. No. 5,210,015 in which the amplification step is carried out in the presence of a detection probe. This detection probe binds under the amplification conditions to the target DNA and contains a reporter and a quencher group. The nuclease activity of the polymerase allows the reporter group to be cleaved from the probe generating a detectable signal. However, this method has the disadvantage of a low sensitivity. In addition the probe must be very carefully selected with regard to its sequence and melting point.

The publication Findlay et al. (Clin. Chem. 39 (1993), 1927–1933) discloses an automated method for the amplification and detection of nucleic acids in which a single reaction vessel with several separate compartments is used wherein the product mixture produced during the amplification in a first compartment has to be transferred into a second separate detection compartment for the detection. A disadvantage of this method is that reaction vessels with a complex construction or/and complicated transfer techniques have to be used.

WO93/10267 describes a method for the amplification and detection of nucleic acids in which a detection probe is present during the reaction which carries an electrochemiluminescent marker group at least at its 3' end so that it cannot serve as a primer for the amplification. A disadvantage of this method is that a complicated construction of detection probes is necessary. Moreover it is not possible to exclude an interference of the amplification reaction by the added detection probe.

EP-A-0 628 568 discloses a method for the amplification and subsequent immobilization or detection of nucleic acids by hybridizing the nucleic acid with a capture probe in which the capture probe is protected against enzymatic extension or/and enzymatic degradation of the hybrid formed. The capture probe can optionally already be present during the amplification reaction. This method also has disadvantages in that the preparation of the protected capture probes is complicated and despite this it is not possible to exclude an interference of the amplification reaction by the capture probe.

An object of the present invention was therefore to provide a method for the amplification and detection of nucleic acids in which the disadvantages of the state of the art are at least partially eliminated. In particular amplification and detection of the nucleic acid should occur in a single device which does not have to be opened during the procedure. In addition the procedure should be rapid, easy to handle, automatable and cheap.

The object according to the invention is achieved by a method for the detection of a nucleic acid comprising:
(a) providing a sample in which it is intended to detect a nucleic acid,
(b) amplifying the nucleic acid in a device in the presence of at least one nucleic acid primer which is specific for the nucleic acid to be detected and at least one capture probe which is specific for the nucleic acid to be detected, the capture probe being immobilized on at least one inner surface of the device and selected in such a way that a hybrid of nucleic acid and capture probe has a lower melting temperature than a hybrid of nucleic acid and primer and wherein the amplification is carried out under such conditions that a hybrid of nucleic acid and primer is stable whereas a hybrid of nucleic acid and capture probe is unstable and
(c) detecting the nucleic acid by binding the amplification products to the immobilized capture probe.

The method according to the invention enables a considerably improved sensitivity to be achieved compared to known methods by selection of a capture probe which, under the amplification conditions, does not hybridize with the primer or/and the nucleic acid to be detected. Moreover there is a minimal contamination risk due to the use of a closed integrated device for amplification and detection. Furthermore the method is simple to carry out and requires no wash steps what-so-ever. Moreover the method according to the invention allows a multiplex amplification e.g. by using various differently labelled primers as well as a multiplex detection e.g. by using different capture probes at defined positions on the surface.

Step (a) of the method according to the invention comprises the provision of a sample which contains the nucleic acid to be detected. The sample can be a natural sample e.g. a body fluid such as blood, serum, plasma, urine or cerebrospinal fluid, a tissue sample or a culture sample and also a sample prepared from a natural sample by process steps. In a preferred embodiment the sample is a natural sample of biological origin which is used to detect a naturally occurring nucleic acid in nucleic acid diagnostics.

Step (b) of the method according to the invention comprises the amplification of the nucleic acid in a suitable device for this. The nucleic acid to be detected can be amplified in any known manner. The amplification is preferably carried out using one or several nucleic acid primers which are sufficiently complementary to the nucleic acid to be detected so that they can form a stable hybrid with the nucleic acid to be detected under the amplification conditions. These primers are preferably extended by an enzyme such as a DNA polymerase that is also present in the reaction mixture. Examples of suitable amplification methods are the ligase chain reaction (LCR) and in particular the polymerase chain reaction (PCR). Furthermore it is preferable that the amplification is carried out with a thermostable enzyme as a thermocyclic reaction in several cycles e.g. 20 to 30 cycles.

The nucleic acid primer present in the method according to the invention is an oligonucleotide or a modified oligonucleotide which is amenable to an enzymatic extension at its 3' end. The length of the nucleic acid primer can be varied over a wide range depending on the requirements and is preferably 15 to 50 nucleotides. The capture probe which is also present during the amplification can also be an oligonucleotide or a modified oligonucleotide e.g. a peptidic nucleic acid. A capture probe is preferably used which does not have a 3' end that is amenable to an enzymatic extension. The capture probe is immobilized on an inner surface of the integrated amplification and detection device. The immobilization can be carried out in any known manner e.g. by covalent coupling or by high affinity biological interactions.

An example of a suitable immobilization method for nucleic acids is to transfer cinnamoylbutyl ether cellulose monolayers onto an inner surface of the detection device using the Langmuir-Blodgett technique. After the film transfer, the monolayers are stabilized by photopolymerization of the olefinic double bonds. Double bonds remaining in the film can be converted by treatment with $OsO_4$ and $NaIO_4$ into aldehyde groups for the subsequent covalent coupling of streptavidin or other substances which are able to immobilize binding partners by high affinity biological interactions e.g. antibodies or lectins. Subsequently the film is contacted with the substance that is to be covalently coupled under suitable conditions e.g. with an aqueous streptavidin solution (10 $\mu$g/ml). Optionally a blocking step with an inert substance e.g. bovine serum albumin can be subsequently carried out.

Capture probes can be immobilized on this surface which contain the complementary binding partner for the high affinity biological interaction e.g. biotin. This immobilization can be achieved by contacting the surface with a solution containing the capture probe (concentration e.g. 200 nmol/l) at 37° C. for 1 hour. The exact procedure for the steps required to produce a surface coated with a capture probe is described for example in Furch et al. (SPIE 2928 (1996), 220–226).

It is essential for the method according to the invention that the primer extension is carried out at a temperature which is higher than the melting temperature of a hybrid between the immobilized capture probe and the nucleic acid to be detected by the method. This results in a significant improvement of the test specificity and sensitivity.

The amplification is particularly preferably carried out at a temperature which is at least 2° C., in particular at least 5° C. and most preferably at least 8° C. higher than the melting point of a hybrid between capture probe and nucleic acid to be detected. The selection of suitable capture probe sequences can be easily carried out with reference to known tables for the stability of nucleic acid hybrids e.g. nucleic acid-nucleic acid hybrids or hybrids between nucleic acids and peptidic nucleic acids.

A further advantage of the method according to the invention is that a multiplex amplification can be carried out. In such a multiplex amplification several different primers can for example be used each of which are provided with different marker groups that can be detected in parallel. In this manner primers that compete with one another for an allele-specific amplification of the nucleic acid to be detected can for example be used as described for example by Lee and Hall (Annals of the Entomological Society of America 89 (1996), 20–27).

Step (c) of the method according to the invention comprises the detection of the amplification products produced in step (b) by binding to the immobilized capture probe. It is expedient to carry out the detection step at a lower temperature than the amplification step i.e. at a temperature at which a stable hybrid between nucleic acid to be detected and capture probe is formed. The detection of the nucleic acid bound to the capture probe can basically be carried out in any manner e.g. by direct measurement of a binding via the layer thickness for example by means of plasmon resonance or by measuring marker groups which are incorporated into the amplification product during the amplification.

The binding of a nucleic acid to the immobilized capture probe is particularly preferably detected by evanescence-induced fluorescence. For this the capture probe is preferably immobilized on an optically transparent inner surface of the device e.g. the well of a microtitre plate. During the amplification fluorescent-labelled nucleotides are then incorporated into the amplification product. This can either be achieved by using fluorescent-labelled primers or/and fluorescent-labelled monomeric dideoxynucleotide triphosphates. An evanescence-induced fluorescence can be detected by a microscope e.g. locally resolved by confocal microscopy, by a scanner or a CCD camera. Time-resolved measurements or real-time measurements are possible.

The detection in the method according to the invention can be carried out as a multiplex detection. In this case several different capture probes can for example be used which are each immobilized at different positions on the surface of the integrated amplification and detection device. In this manner it is for example possible to carry out a mutation analysis of the nucleic acid to be detected especially if the detection is carried out using differential hybridization conditions between the nucleic acid to be detected and the capture probes e.g. by controlled temperature increase.

Examples of optically transparent materials to which the capture probe can be immobilized are organic or inorganic, optically transparent materials such as glass, quartz, silicon, plastics such as polycarbonate, acrylic polymers or polystyrene. The immobilization of the capture probe on the surface of the reaction device is a thermostable immobilization so that no significant detachment of the capture probe occurs at the temperatures that prevail during the amplification reaction. On the one hand the probe can be immobilized on the solid phase by covalent immobilization techniques. On the other hand and preferably the immobilization can be achieved by means of a high affinity binding pair e.g. streptavidin/biotin.

The detection of nucleic acids by evanescence-induced fluorescence is already known (cf e.g. EP-A-0 245 206; WO96/09532) and explicit reference is made to these known methods. However, it was surprisingly found that particularly sensitive and reliable test results can be obtained by the method according to the invention which comprises a combination of an amplification reaction in the presence of an immobilized, non-interfering capture probe and the detection of the amplification product by evanescent-induced fluorescence.

A further subject matter of the present invention is a reagent kit for the detection of nucleic acids comprising:

(a) a device for the amplification and detection of nucleic acids containing at least one capture probe immobilized on at least one inner surface thereof, (b) at least one nucleic acid primer, (c) optionally deoxyribonucleotides and (d) optionally a suitable enzyme for extending the nucleic acid primer, wherein the capture probe is selected such that a hybrid of the nucleic acid to be detected and the capture probe has a lower melting temperature than a hybrid of the nucleic acid to be detected and primer.

The device is preferably a closed system which enables an integrated amplification and detection of a nucleic acid present in a sample. Examples of suitable amplification and detection devices are reaction vessels e.g. microreaction vessels with a volume of up to 100 µl such as microtitre plates. In addition other devices such as biosensors e.g. chips can also of course be used. The capture probe is preferably immobilized on an optically transparent surface of the device. The kit preferably contains a fluorescent label, for example a labelled nucleic acid primer or/and labelled deoxyribonucleotides. The enzyme contained in the kit is preferably a thermostable DNA polymerase e.g. Taq polymerase.

Yet a further aspect of the present invention is a method for the detection of a nucleic acid comprising:

(a) providing a sample in which it is intended to detect a nucleic acid, (b) amplifying the nucleic acid in a closed device in the presence of at least one nucleic acid primer which is specific for the nucleic acid to be detected and at least one capture probe which is specific for the nucleic acid to be detected wherein the capture probe is immobilized on at least one optically transparent inner surface of the device and wherein fluorescent labels are incorporated into the amplification product and (c) detecting the nucleic acid by binding the amplification products to the immobilized capture probe by means of evanescence-induced fluorescence.

The present invention also concerns a reagent kit for the detection of nucleic acids comprising:

(a) a device for the amplification and detection of nucleic acids containing at least one capture probe immobilized on a transparent inner surface thereof, (b) at least one nucleic acid primer, (c) optionally deoxyribonucleotides, (d) optionally an enzyme suitable for the extension of the nucleic acid primer (e) a fluorescent label and (f) optionally a means for the detection of amplification products by evanescence-induced fluorescence.

This reagent kit is also preferably used for the integrated amplification and detection of nucleic acids in a closed system. Preferred features of the method and reagent kit are as stated above for the first aspect of the invention.

What is claimed is:

1. A method for detection of a nucleic acid comprising:

(a) providing a sample in which it is intended to detect a nucleic acid, (b) amplifying the nucleic acid in a closed device in the presence of at least one nucleic acid primer which is specific for the nucleic acid to be detected and at least one capture probe which is specific for the nucleic acid to be detected, the capture probe being immobilized on at least one inner surface of the device and selected in such a way that a hybrid of nucleic acid and capture probe has a lower melting temperature than a hybrid of nucleic acid and primer and wherein the amplification is carried out under such conditions that a hybrid of nucleic acid and primer is stable whereas a hybrid of nucleic acid and capture probe is unstable, thereby forming an amplification product, (c) binding the amplification product to the immobilized capture probe, and (d) detecting the binding of the amplification product to the capture probe by evanescence-induced fluorescence, wherein said closed device is closed during the entire amplifying and detecting procedure.

2. Method as claimed in claim 1, wherein the amplification and detection are carried out in a single device which is not opened during the reaction.

3. Method as claimed in claim 1, wherein the capture probe is immobilized on an optically transparent inner surface of the device.

4. Method as claimed in claim 1 to 3, wherein the fluorescent labels are incorporated into the amplification product.

5. Method as claimed in claim 1, wherein a binding of the amplification products to the capture probe is detected by means of evanescence-induced fluorescence.

6. Method as claimed in claim 1, wherein an immobilized capture probe is used that is selected from nucleic acids and peptidic nucleic acids.

7. Method as claimed in claim 1, wherein the reaction is carried out in a microtitre plate well.

8. Method as claimed in claim 1, wherein different capture probes are each immobilized at different positions of the device.

9. Method as claimed in claim 1, wherein various differently labelled primers are used.

10. A reagent kit for detection of nucleic acids comprising:

(a) a closed device for the amplification and detection of nucleic acids containing at least one capture probe immobilized on at least one inner surface thereof, (b) at least one nucleic acid primer, (c) optionally deoxyribonucleotides, (d) optionally a suitable enzyme for extending the nucleic acid primer, wherein the capture probe is selected such that a hybrid of the nucleic acid to be detected and the capture probe has a lower melting temperature than a hybrid of the nucleic acid to be detected and primer, (e) a means for sealing said device during said amplification and detection, and (f) a means for detecting binding of the nucleic acids to the capture probe by evanescence-induced fluorescence.

11. Kit as claimed in claim 10, wherein the capture probe is immobilized on an optically transparent surface of the device.

12. Kit as claimed in claim 10, wherein the device represents a closed system.

13. Kit as claimed in claim 10, wherein it contains a fluorescent label.

14. Kit as claimed in claim 10, wherein the enzyme is a thermostable DNA polymerase.

15. A method for detection of a nucleic acid comprising:
(a) providing a sample in which it is intended to detect a nucleic acid,
(b) amplifying the nucleic acid in a closed device in the presence of at least one nucleic acid primer which is specific for the nucleic acid to be detected and at least one capture probe which is specific for the nucleic acid to be detected, wherein the capture probe is immobilized on at least one optically transparent inner surface of the closed device and fluorescent labels are incorporated into an amplification product, and
(c) detecting the nucleic acid by binding the amplification product to the immobilized capture probe by means of evanescence-induced fluorescence,
wherein said closed device is closed during the entire amplifying and detecting procedure.

16. A reagent kit for detection of nucleic acids comprising:
(a) a closed device for the amplification and detection of nucleic acids containing at least one capture probe immobilized on at least one inner surface thereof,
(b) at least one nucleic acid primer,
(c) optionally deoxyribonucleotides,
(d) optionally an enzyme suitable for the extension of the nucleic acid primer,
(e) a fluorescent label,
(f) optionally a means for detection of amplification products by evanescence-induced fluorescence,
(g) a means for sealing said device during said amplification and detection.

\* \* \* \* \*